United States Patent
Vähäsalo et al.

(10) Patent No.: US 12,332,174 B2
(45) Date of Patent: Jun. 17, 2025

(54) METHOD AND SYSTEM FOR DETERMINATION OF STARCH IN A SAMPLE

(71) Applicant: KEMIRA OYJ, Helsinki (FI)

(72) Inventors: Lari Vähäsalo, Littoinen (FI); Marjatta Piironen, Oulu (FI); Iiris Joensuu, Espoo (FI)

(73) Assignee: KEMIRA OYJ, Helsinki (FI)

( * ) Notice: Subject to any disclaimer, the term of this patent is extended or adjusted under 35 U.S.C. 154(b) by 1196 days.

(21) Appl. No.: 16/089,841

(22) PCT Filed: Mar. 24, 2017

(86) PCT No.: PCT/FI2017/050206
§ 371 (c)(1),
(2) Date: Sep. 28, 2018

(87) PCT Pub. No.: WO2017/168045
PCT Pub. Date: Oct. 5, 2017

(65) Prior Publication Data
US 2020/0278293 A1    Sep. 3, 2020

(30) Foreign Application Priority Data
Mar. 31, 2016 (FI) .................. 20165270

(51) Int. Cl.
*G01N 21/53* (2006.01)
*G01N 15/14* (2024.01)
(Continued)

(52) U.S. Cl.
CPC ....... *G01N 21/532* (2013.01); *G01N 15/1434* (2013.01); *G01N 21/59* (2013.01);
(Continued)

(58) Field of Classification Search
CPC .............................................. G01N 21/77–83
See application file for complete search history.

(56) References Cited

U.S. PATENT DOCUMENTS

| | | |
|---|---|---|
| 7,604,712 B2 | 10/2009 | Trung et al. |
| 2006/0196622 A1 | 9/2006 | Trung et al. |

(Continued)

FOREIGN PATENT DOCUMENTS

| | | |
|---|---|---|
| CN | 1610827 A | 4/2005 |
| CN | 101133315 A | 2/2008 |

(Continued)

OTHER PUBLICATIONS

Rice, Matthew. 2001. "New Techniques for Continuous Chemical Analysis in the Pulp & Paper Industry" PhD diss., Royal Institute of Technology. https://www.diva-portal.org/smash/get/diva2:8895/FULLTEXT01.pdf. (Year: 2001).*

(Continued)

*Primary Examiner* — Elizabeth A Robinson
*Assistant Examiner* — Brittany I Fisher
(74) *Attorney, Agent, or Firm* — Espatent Oy

(57) ABSTRACT

In a starch concentration measurement, a liquid sample is conducted from a liquid sample such as pulp suspension or filtrate of a paper, board or tissue process. An iodine solution is added to the sample, and a light absorbance or transmittance of the sample is measured at a wavelength longer than about 650 nm, for example longer than about 700 nm. The measured absorbance or transmittance of the sample is (Continued)

converted into the starch concentration of the sample by a predefined correlation between a starch concentration and a light absorbance or transmittance.

17 Claims, 7 Drawing Sheets

(51) Int. Cl.
    *G01N 15/1434*     (2024.01)
    *G01N 21/07*     (2006.01)
    *G01N 21/59*     (2006.01)
    *G01N 21/77*     (2006.01)
    *G01N 21/84*     (2006.01)
    *G01N 33/34*     (2006.01)

(52) U.S. Cl.
    CPC ............. *G01N 21/77* (2013.01); *G01N 21/84* (2013.01); *G01N 33/343* (2013.01); *G01N 2015/1486* (2013.01); *G01N 2021/8416* (2013.01); *G01N 2201/121* (2013.01)

(56) References Cited

U.S. PATENT DOCUMENTS

| 2008/0241932 A1 | 10/2008 | Kendig |
| 2009/0320570 A1 | 12/2009 | Wiese |
| 2015/0114094 A1 | 4/2015 | Vähäsalo |
| 2015/0147814 A1 | 5/2015 | Joensuu et al. |

FOREIGN PATENT DOCUMENTS

| CN | 101665786 A | | 3/2010 |
| CN | 101839849 A | | 9/2010 |
| CN | 102495052 A | | 6/2012 |
| CN | 102539796 A | | 7/2012 |
| CN | 102552376 A | | 7/2012 |
| CN | 102706826 A | * | 10/2012 |
| CN | 104833671 A | * | 8/2015 |
| EP | 2376897 A4 | | 10/2017 |
| JP | 2003530891 A | | 10/2003 |
| JP | 2010043023 A | | 2/2010 |
| JP | 2015055549 A | | 3/2015 |
| WO | 01-81617 A1 | | 11/2001 |
| WO | 03056327 A1 | | 7/2003 |
| WO | 2005-003311 A9 | | 1/2005 |
| WO | 2010-069017 A1 | | 6/2010 |
| WO | 2013/175077 A1 | | 11/2013 |

OTHER PUBLICATIONS

"Guidelines for Calibration in Analytical Chemistry", Pure Appl. Chem. 70 (1998) 993-1014. (Year: 1998).*
Bridgeman, Jonathan, J. S. Simms, and S. A. Parsons. "Practical and theoretical analysis of relationships between particle count data and turbidity." Journal of Water Supply: Research and Technology—AQUA 51, No. 5 (2002): 263-271. (Year: 2002).*
Banks, W., C. T. Greenwood, and D. D. Muir. "The Characterization of Starch and Its Components. Part 6. A Critical Comparison of the Estimation of Amylose-Content by Colorimetric Determination and Potentiometric Titration of the Iodine-Complex." Starch-Stärke 26, No. 3 (1974): 73-78. (Year: 1974).*
Silverman, Leslie, and Frederick J. Viles Jr. "The determination of cotton textile dusts in air." Textile Research Journal 20, No. 2 (1950): 109-122. (Year: 1950).*
Foster, Joseph F., and Melvin D. Sterman. "A light scattering investigation of the retrogradation of amylose." Journal of Polymer Science 21, No. 97 (1956): 91-101. (Year: 1956).*
First Office Action issued on Sep. 27, 2020, by the Chinese Patent Office in corresponding Chinese Patent Application No. 201780028180.6, and an English Translation of the Office Action. (16 pages).
Finnish Search Report dated Oct. 12, 2016, issued by the Finnish Patent and Registration Office in the corresponding Finnish Patent Applicantion No. 20165270.
International Search Report (PCT/ISA/210) mailed on Jul. 5, 2017, by the European Patent Office as the International Searching Authority for International Application No. PCT/FI2017/050206.
Written Opinion (PCT/ISA/237) mailed on Jul. 5, 2017, by the European Patent Office as the International Searching Authority for International Application No. PCT/FI2017/050206.
Vähäsalo, L. et al.,"Reliable spectrophotometric determination of starch concentration in papermaking process water", Nordic Pulp and Paper Research Journal, No. 1, pp. 75-77, 2004.
Bernal-Uruchurtu, M.I. et al., "Structure, spectroscopy and dynamics of halogen molecules interacting with water", International Reviews in Physical Chemistry, No. 2, pp. 223-265, 2009.
Office Action issued on Aug. 3, 2020, by the Taiwanese Patent Office in corresponding Taiwanese Patent Application No. 106109785, and an English Translation of the Office Action. (20 pages).

* cited by examiner

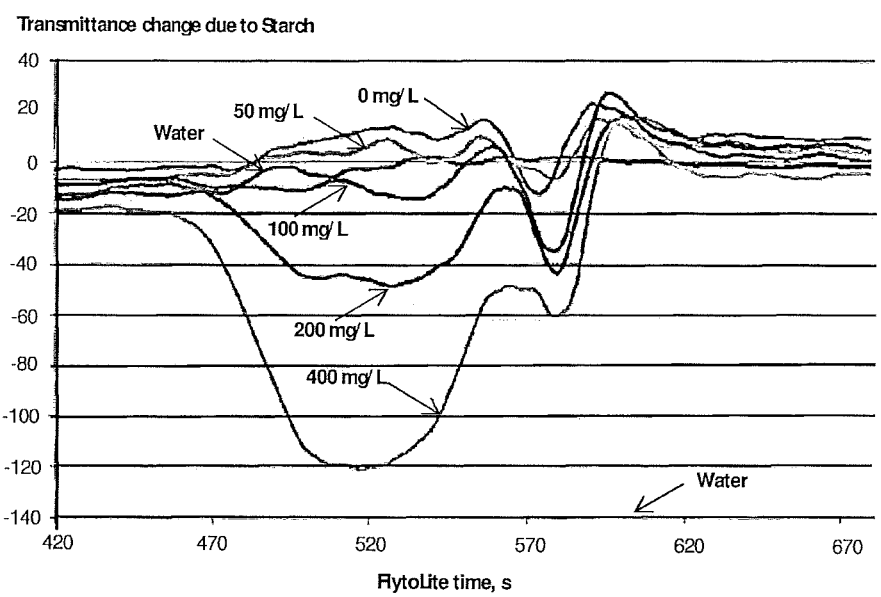
FIG. 14
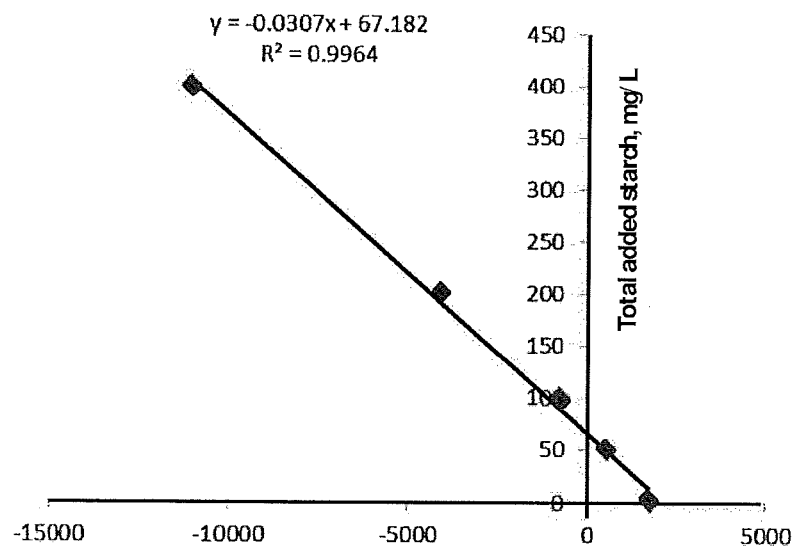
FIG. 15   Summarized transmittance change due to Starch

METHOD AND SYSTEM FOR DETERMINATION OF STARCH IN A SAMPLE

FIELD OF THE INVENTION

The invention relates to measurement technology of industrial liquids containing starch. In particular, the invention presents the method and system for online monitoring of starch concentration in suspensions and/or filtrates in forest industry.

BACKGROUND OF THE INVENTION

Starch is commonly used in paper, e.g. to increase paper strength. However, soluble starch is an interfering substance that can cause severe runnability and microbial problems, and papermakers should therefore try to minimize the starch concentration in the process waters. Starch which has been adsorbed onto fibers and other particles, i.e. an adsorbed starch, is not a problem for the papermaker but could be of interest.

Starch can for example be analyzed by gas chromatography after hydrolysis into monomeric glucose. However, this is a very time consuming process. The most common fast measurement of dissolved starch is the classical iodine starch method. The method is based on the reaction between iodine/potassium iodide and starch. Iodine/potassium iodide changes color when combined with amylose and amylopectin with absorption maxima at 605 nm (nanometers) and 530 nm, respectively. Traditionally the absorbance is measured at 580 nm, which is the overall maxima of common wet end starches. However, the light absorption is to some extent dependent on the degree of modification of starch. Therefore, the Iodine method needs to be calibrated for different starches independently. The basic idea is to make a linear regression calibration between known amounts of starch and the absorbance at 580 nm.

Another drawback with the Iodine method is that the turbidity of the samples is not taken into account, making the method unpredictable if turbidity varies. This problem is much more severe in processes where coated broke or fillers are used than in systems without any pigment. Vähäsalo L. et al., "Reliable spectrophotometric determination of starch concentration in papermaking process waters, Nord. Pulp Pap. Res. J., 19:1, 2004, pages 75-77, found that the traditional univariate iodine starch method is unreliable for samples with varying turbidity. However, the absorption spectrum between 500 nm and 900 nm contains the information needed for a reliable analysis method using multivariate calibration. FIG. 1A shows the true and measured amount of starch in papermaking samples with the traditional iodine method. The samples were filtered by either a 200-mesh wire or a black ribbon paper filter. All dots should be on the black line. It is clear that the traditional iodine method does not work. However, instead of using a one variable calibration method Vahasalo et al showed that one can use the whole measured absorption spectra and a multivariate calibration technique and optimally get the results shown in FIG. 1B.

Thus the traditional spectrophotometric method for determination of starch in a sample has a few vital drawbacks such as the effect of turbidity and variations in the absorbance of different starches. There is a need for fast and reliable analysis methods for starch.

BRIEF DESCRIPTION OF THE INVENTION

An aspect of the invention is a method of analyzing starch concentration in a liquid sample, a method of controlling a process, a measurement system, and a control system according to the attached independent claims.

A method includes:
conducting a sample of liquid from a process stream of liquid for online analysis of a starch concentration in the process stream of liquid based on the sample of liquid;
adding iodine solution to the sample of liquid;
measuring a light absorbance or transmittance of the sample of liquid after the step of adding the iodine solution;
converting the measured absorbance or transmittance of the sample of liquid into the starch concentration of the sample of liquid by a predefined correlation between a starch concentration and a light absorbance or transmittance; and
eliminating an influence of unreacted iodine on the measured light absorbance or transmittance in the starch concentration analysis by measuring the light absorbance or transmittance of the sample of liquid at a wavelength longer than about 700 nanometers.

Embodiments of the invention are recited in the dependent claims.

An aspect of the invention is a method of analyzing starch concentration in a liquid sample, comprising
conducting a sample from a stream of liquid,
adding iodine solution to the sample,
measuring a light absorbance or transmittance of the sample after the step of adding the iodine solution,
converting the measured absorbance or transmittance of the sample of liquid into the starch concentration of the sample by means of a predefined correlation between a starch concentration and a light absorbance or transmittance, wherein the light absorbance or transmittance is measured at a wavelength longer than about 650 nanometers, preferably longer than about 700 nanometers.

An aspect of the invention is a method comprising:
conducting a sample of liquid from a process stream of liquid for online analysis of a starch concentration in the process stream of liquid based on the sample of liquid;
adding iodine solution to the sample of liquid;
measuring a light absorbance or transmittance of the sample of liquid both before and after adding the iodine solution to provide two measurements;
converting a difference between the two measurements of measured absorbance or transmittance of the sample of liquid into the starch concentration of the sample by a predefined correlation between a starch concentration and a light absorbance or transmittance; and
eliminating an influence of unreacted iodine on the measured light absorbance or transmittance in the starch concentration analysis by measuring the light absorbance or transmittance of the sample of liquid at a wavelength longer than about 700 nanometers.

Another aspect of the invention a method of analysing starch concentration in a liquid sample, comprising
conducting a sample from a stream of liquid,
adding iodine solution to the sample,
measuring a light absorbance or transmittance of the sample both before and after the step of adding the iodine solution,
converting a difference between the two measured absorbance or transmittance of the sample into the starch concentration of the sample by means of a predefined correlation between a starch concentration and a light absorbance or transmittance, wherein the light absorbance or transmittance is measured at a wavelength longer than about 650 nanometers, preferably longer than about 700 nanometers.

In an embodiment, the method comprises
separating the sample is separated into one or more particle populations according to a particle size before the step of adding the iodine solution,
measuring the light absorbance or transmittance of the sample for each particle population of the sample,
converting the measured absorbance or transmittance of the sample into the starch concentration of the sample for each particle population by means of the predefined correlation between the starch concentration and the light absorbance or transmittance.

In an embodiment, the method comprises
separating the sample into one or more particle populations according to a particle size before the step of adding the iodine solution,
measuring the light absorbance or transmittance of the sample for each particle population of the sample both before and after the step of adding the iodine solution,
converting a difference between the two measured absorbance or transmittance of the sample into the starch concentration of the sample for each particle population by means of the predefined correlation between the starch concentration and the light absorbance or transmittance.

In an embodiment, the method comprises
measuring a light scattering of the sample before and/or after the step of adding the iodine solution,
compensating an effect of turbidity of the sample on the measurement of the absorbance or transmittance based on the light scattering measurement.

In an embodiment, the one or more particle population comprises a population containing dissolved starch without particulate matter.

In an embodiment, the method comprises determining a ratio of dissolved and absorbed starch in the sample based on the starch concentrations of the one or more particle populations.

In an embodiment, the method comprises
measuring a light scattering of the sample before and/or after the step of adding the iodine solution,
determining a particle count in the sample based on the measured light scattering.

In an embodiment, the one or more particle populations include one or more of colloids, fines, fibers, floccules and agglomerates.

In an embodiment, the chemical liquid sample is conducted from a pulp suspension or filtrate in a paper, board or tissue process.

An aspect of the invention is a method of controlling a paper, board or tissue process, said control utilizing a starch concentration analyzed with the analyzing method.

In an embodiment, the control includes one or more of retention control, sizing control, strength control, deposit control and microbe control.

An aspect of the invention is a measurement system implementing the analyzing method.

An aspect of the invention is a process control system comprising an online analyzer system implementing the analyzing method the process control system being configured to control a paper, board or pulp process based on starch measurement results from the online analyzer system.

BRIEF DESCRIPTION OF THE DRAWINGS

In the following exemplary embodiments of the invention will be described with reference to the attached drawings, in which

FIG. 14 shows transmittance change at 754 nm as a function of starch; and

FIG. 15 shows the true starch amount as a function of transmittance change.

EXEMPLARY EMBODIMENTS

As discussed above, a significant drawback of the traditional spectrophotometric method for determination of starch in a sample is variation in the absorbance of different starches. Traditional spectrophotometric determination of starch concentration in a water sample is typically done by adding a known amount of iodine in the sample and a reference cell or alternatively using a blank sample with water and iodine for base line correction. Traditionally the absorbance of iodine/starch complex is measured at a wavelength of 580 nm which is the overall maxima of common wet end starches. However, the light absorption is to some extent dependent on the degree of modification of starch. Therefore, the Iodine method needs to be calibrated for different starches independently. In other words, traditional starch iodine method requires that a calibration curve be constructed for each different type of starch.

According to an aspect of the invention, a light absorbance or transmittance of the sample after adding the iodine solution may be measured at a wavelength longer than about 650 nm, preferably longer than about 700 nm.

Figure 1A:
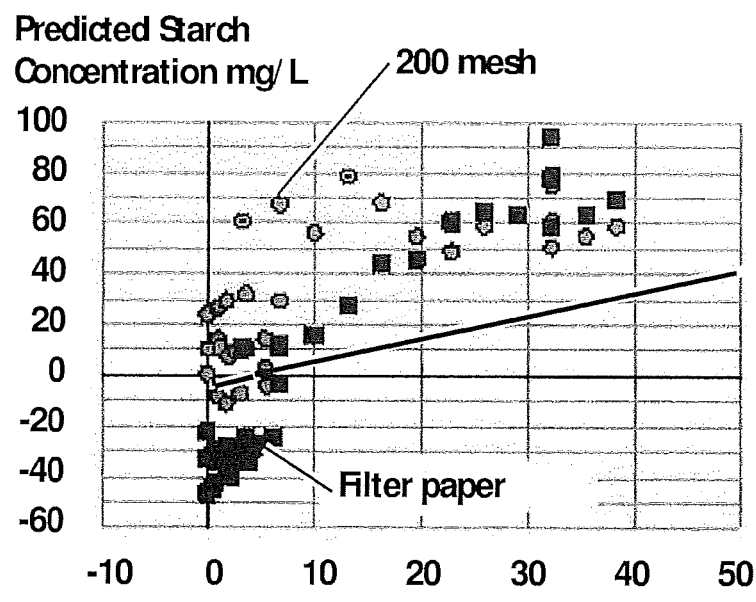
FIG. 1A shows the true and measured concentration of starch with the traditional iodine method.
Figure 1B:
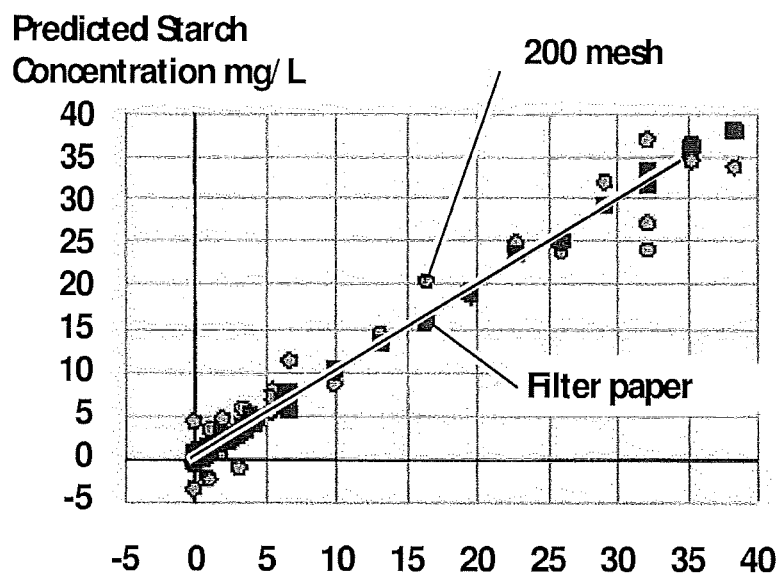
FIG. 1B shows the true and measured concentration of starch when using multivariate calibration.
Figure 2:
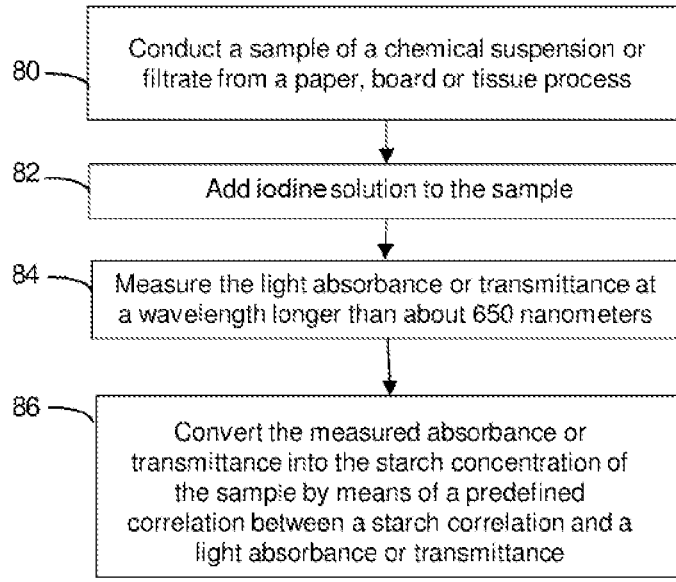
FIG. 2 shows a flow diagram of a method for measuring starch concentration in a liquid sample such as pulp suspension or filtrate in a paper, board or tissue process according to an exemplary embodiment of the invention.

An exemplary embodiment of a method for measuring starch concentration in a liquid sample such as pulp suspension or filtrate in a paper, board or tissue process is illustrated in FIG. 2. A sample is provided from a liquid sample such as pulp suspension or filtrate of a paper, board or tissue process (step 20). An iodine solution is added to the sample (step 22). A light absorbance or transmittance of the sample is measured at a wavelength longer than about 650 nm, preferably longer than about 700 nm, after adding the iodine solution (step 24). The measured absorbance or transmittance of the sample is converted into the starch concentration of the sample by means of a predefined correlation between a starch concentration and a light absorbance or transmittance (step 26).

The inventors have found that by the use of a higher wavelength the calibration curve between absorption and starch concentration is not affected by the starch type or the degree of modification of the starch. This is based on the fact that by using a higher wavelength, i.e. a wavelength longer than about 650 nm, preferably longer than about 700 nm, where unreacted iodine does not adsorb light, a reference cell or a blank sample is not needed. Measurements are not made at wavelengths shorter than about 650 nm, preferably shorter than about 700 nm. The aspect of the invention does not require that a calibration curve be constructed for each different type of starch, unlike in the traditional starch iodine method with the measurement at a wavelength of 580 nm which is the overall maxima of common wet end starches. The aspect of the invention further simplifies the measurement of starch concentration as the amount of iodine added to the sample is not critical as long as it is sufficient to react with all starch in the sample. Therefore, the exact amount of the iodine solution need not be known, unlike in the traditional starch iodine method. Further, the prior art multivariate calibration method is not needed that requires measurement over a whole absorption spectrum between 500 nm and 900 nm to have the sufficient information for a reliable analysis. The phrase "measurement at a wavelength" as used herein preferably refers to a measurement at one wavelength with a spectral resolution set by a measurement arrangement in question, or refers to a measurement of a narrow spectra of wavelengths longer than about 650 nm, preferably longer than about 700 nm and eliminating an influence of unreacted iodine on the measured light absorbance or transmittance in the starch concentration analysis.

In the following the traditional way of measuring starch and a new method according to embodiments of the invention are investigated by means of examples in which three different starches were used, a native starch, a cationic wet-end starch and a starch based fixing agent.

For the investigation, a 0.1 M Iodine solution was prepared by mixing 20 grams of potassium iodide and 6.4 grams of iodine in 500 mL (millilitre) of distilled water. A ratio of 75 µL (microlitres) of Iodine solution to 1 mL of sample was used if not otherwise noted. In a laboratory spectrometer distilled water was used in the reference cell.

Figure 3:
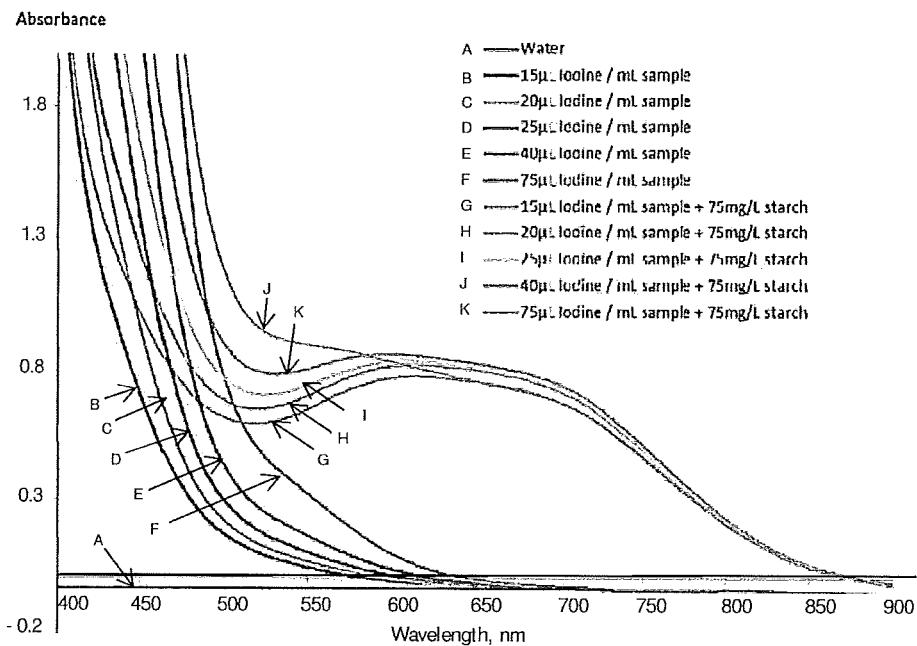
FIG. 3 shows the light absorbance spectra of iodine-starch complex as a function of iodine solution with and without starch.

In FIG. 3 we show the measured light absorption of starch as a function of Iodine solution in water samples over the spectra from 400 nm to 900 nm. The first absorption curve A is for pure water. Next absorption curves B, C, D, E and F are for pure iodine iodine-water solutions (without starch) with concentrations 15 µL/mL (microliters/millilitre), 20 µL/mL, 25 µL/mL, 40 µL/mL, and 75 µL/mL, respectively. It can be noted that iodine in water only starts to absorb light at wavelengths below approximate 700 nm for any iodine concentrations, and that the absorbance of light is not significant until at wavelengths below approximately 650 nm.

Referring again to FIG. 3, absorption curves G, H, I, J, and K are for samples with 75 mg/mL starch and with different iodine concentrations 15 µL/mL (microliters/millilitre), 20 µL/mL, 25 µL/mL, 40 µL/mL, and 75 µL/mL, respectively. It can be seen that the amount of iodine starts to significantly affect to the absorbance of the sample at wavelengths below 650 nm. On the other hand, at wavelengths above approximately 650 nm, and especially above approximately 700 nm, the absorbance curves are very similar. Further, the results clearly show that the ratio of 75 µL of Iodine solution to 1 mL of sample is more than enough for enabling absorbance measurement of all samples. There was almost identical absorption with as low as 15 µL of iodine.

Figure 4:
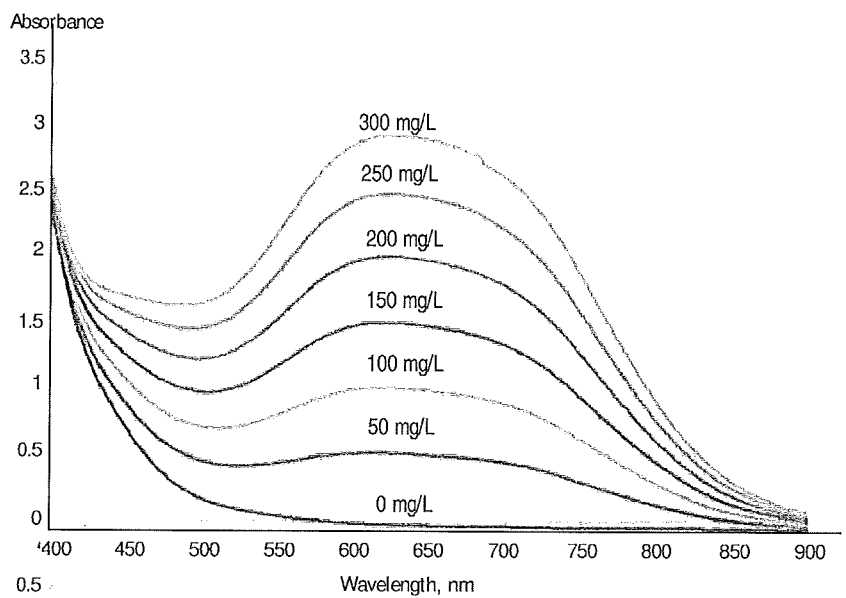
FIG. 4 shows the light absorbance spectra of Iodine-Starch complex as a function of starch concentration.

The light absorbance of Iodine-Starch complex as a function of starch was measured with the laboratory spectrometer and is shown in FIG. 4. The amounts of starch in samples were 0 mg/L (milligrams/litre), 50 mg/L, 100 mg/L, 150 mg/L, 200 mg/L, 250 mg/L, and 300 mg/L. Even if the absorbance for the higher amounts of starch was very high, a linear correlation between the amount of starch and the absorbance value could be found at any wavelength between 500 nm and 850 nm.

Figure 5:
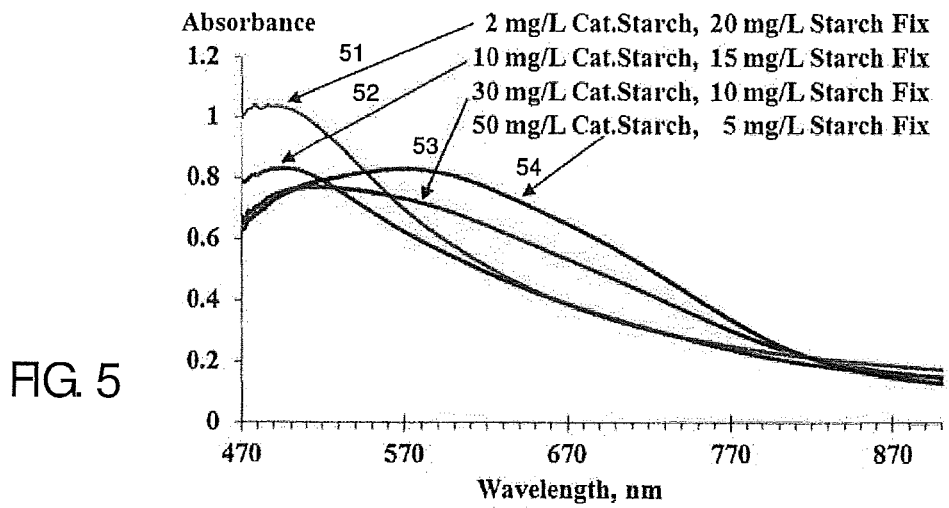
FIG. 5 shows the absorption spectrum of mixtures of two different starch types.

As mentioned different starches give different absorption spectra. Typically the 580 nm is the maximum even if the absorption level will change as a function of starch modification. However, there are starches which have highly distorted absorption spectra from this general rule, one such is a starch base fixing agent. FIG. 5 shows the absorption spectrums for four mixtures of two different starch types. The first sample 51 contains a mixture of 2 mg/L cationic starch and 20 mg/L starch base fixing agent, the second sample 52 contains a mixture of 10 mg/L cationic starch and 15 mg/L starch base fixing agent, the third sample 53 contains a mixture of 30 mg/L cationic starch and 10 mg/L starch base fixing agent, and the fourth sample 54 contains a mixture of 50 mg/L cationic starch and 5 mg/L starch base fixing agent.

Figure 6:
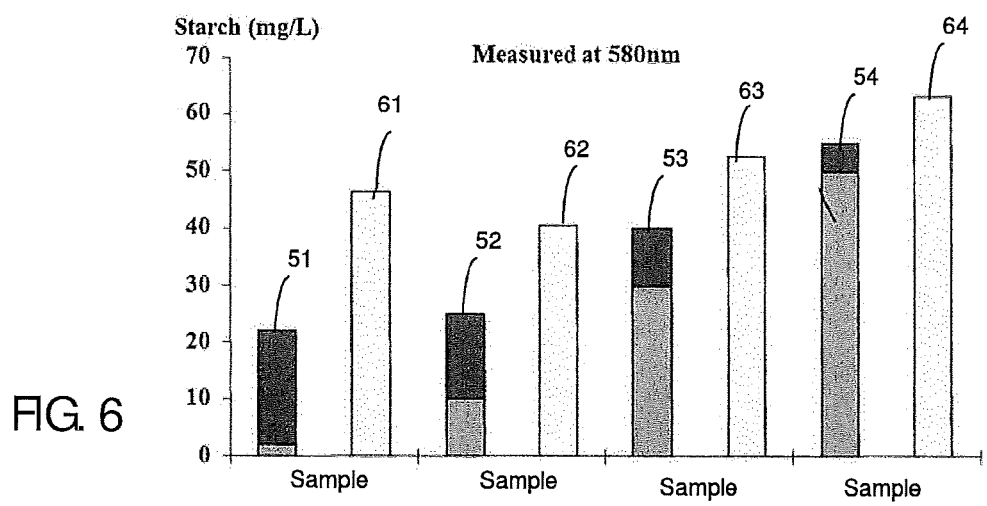
FIG. 6 shows the predicted amount of starch using the calibration curve at 580 nm for samples of FIG. 5.

FIG. 6 shows the predicted amount of starch using the traditional method of measuring the absorption at 580 nm for the samples in FIG. 5. The calibration curve was constructed using cationic starch. In FIG. 6, columns 51, 52, 53, and 54 show the true amounts of starch in the samples, the lighter colour presenting the amount of cationic starch and the darker colour presenting the amount of the starch base fixing agent. Columns 61, 62, 63, and 64 show respective predicted amounts of starch calculated based on absorption measured at 580 nm. It can be seen that there is a significant difference or error between the true and predicted amounts of starch. In other words, if a sample contains different types of starches such as cationic and native starch, the prediction of the amount of starch will fail with the traditional method.

Figure 7:
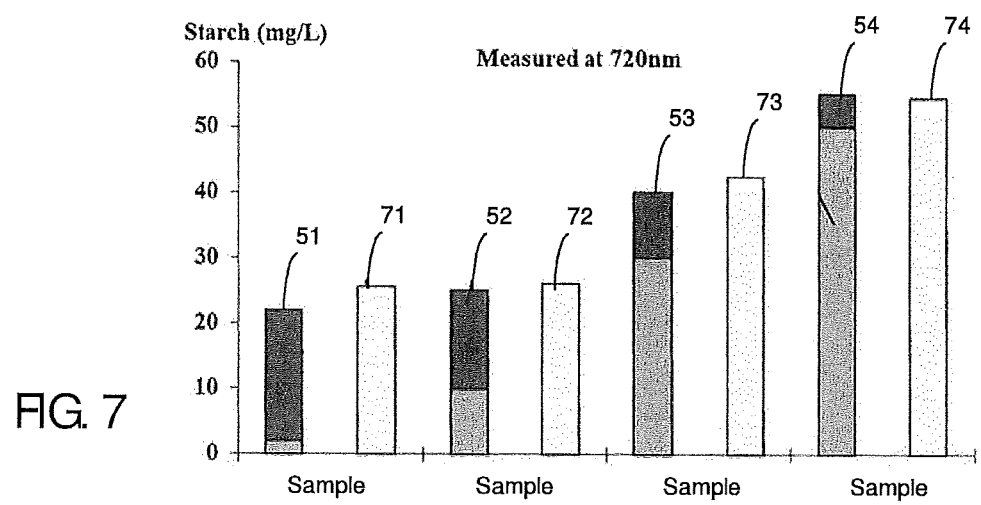
FIG. 7 shows the predicted amount of starch using the calibration curve at 720 nm for sampled of FIG. 5.

FIG. 7 shows the predicted amount of starch using the calibration curve at 720 nm for samples of FIG. 5. In FIG. 7, columns 51, 52, 53, and 54 show the true amounts of starch in the samples, the lighter colour presenting the amount of cationic starch and the darker colour presenting the amount of the starch base fixing agent. Columns 71, 72, 73, and 74 show respective predicted amounts of starch calculated based on absorption measured at 720 nm. It can be seen that there is the predicted amounts of starch correspond to the true amounts of the samples quite accurately. In other words, using the higher wavelengths according to embodiments of the invention, the prediction of the amount of starch can be accurately made for samples with varying mixtures of different starch types.

According to another aspect of the invention, a light absorbance or transmittance of the sample is measured at a wavelength longer than about 650 nm, preferably longer than about 700 nm both before and after adding an iodine solution to a sample, in which case the difference of the two measurements is related to the starch and can be utilized as a measure for the starch concentration of the sample. The baseline shift due to the turbidity is present in both measurements but cancelled from the difference of the measurements. Thereby the problem regarding the baseline shift due to turbidity can be mitigated or avoided. This is especially important in applications where the ratio of iodine-to-sample cannot be fully controlled, such as in an on-line analyzer. It should be noted that the type of cancelling the effect of turbidity is made possible by the use of longer wavelengths of light in accordance with aspects of the invention. As mentioned above, unreacted iodine absorbs light at 580 nm which would cause an absorption increase even in plain water.

Figure 8:
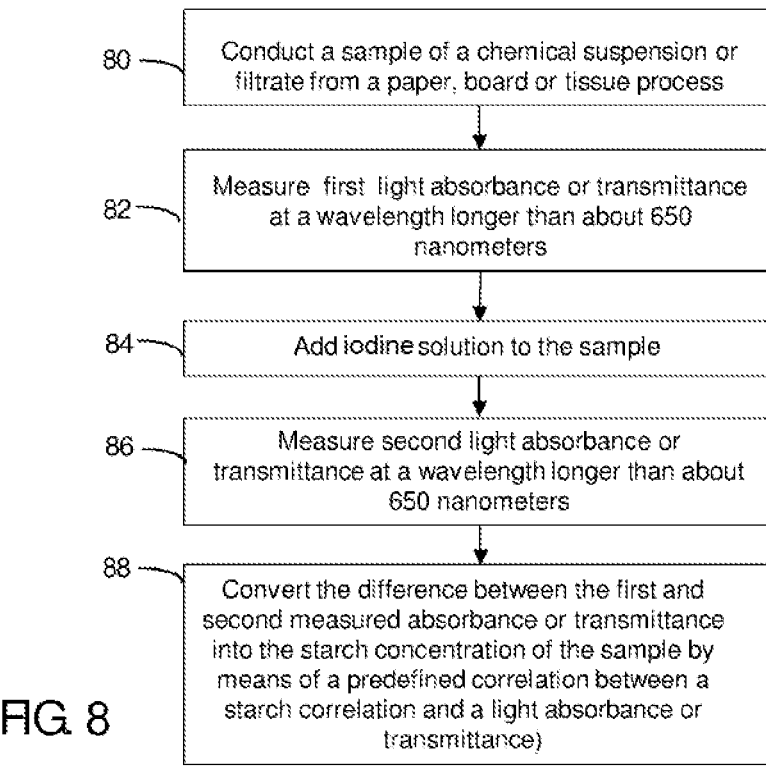
FIG. 8 shows a flow diagram of a method for measuring starch concentration in a liquid sample such as pulp suspension or filtrate in a paper, board or tissue process according to another exemplary embodiment of the invention.

An exemplary embodiment of a method for measuring starch concentration in a liquid sample such as pulp suspension or filtrate in a paper, board or tissue process is illustrated in FIG. 8. A sample is provided from a liquid sample such as pulp suspension or filtrate of a paper, board or tissue process (step 80). A first light absorbance or transmittance of the sample is measured at a wavelength longer than about 650 nm, preferably longer than about 700 nm (step 82). After the measurement, an iodine solution is added to the sample (step 84). A second light absorbance or transmittance of the sample is measured at a wavelength longer than about 650 nm, preferably longer than about 700 nm, after adding the iodine solution (step 86). A difference between the first and second measured absorbance or transmittance of the sample is converted into the starch concentration of the sample by means of a predefined correlation between a starch concentration and a light absorbance or transmittance (step 88).

Figure 9:
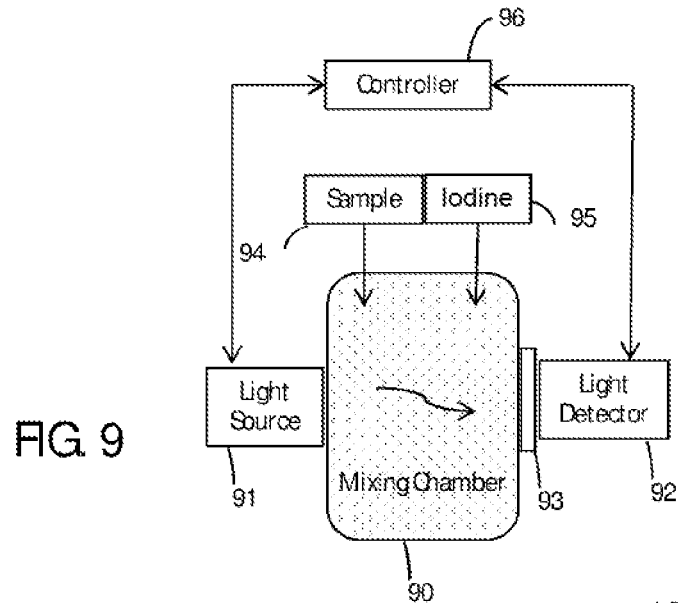
FIG. 9 shows a schematic block diagram of measurement equipment according to an exemplary embodiment.

A method according to embodiments of the invention can be used in offline and online measurements in a laboratory, a plant or a mill, for example. FIG. 9 shows a schematic block diagram of exemplary measurement equipment according to an embodiment of the invention. A light source 91 and a light detector 92 are arranged to the opposite sides of a mixing chamber 90. The light detector 92 may be provided with a light filter 93 that allows only a light of the desired longer wavelength (e.g. 740 nm) or wavelengths to reach the light detector. Alternatively, the filter 93 may be provided at another location on the optical path between the light source 91 and the light detector 92, or the light source and/or the light detector may be configured to operate at the desired longer wavelength(s). The chamber 90 may be, for example, a beaker protected from light and provided with a magnetic mixer. Further, the mixing chamber 90 is provided with a sample inlet device 94 and an iodine solution inlet device 95. The measurement equipment is controlled by a controller 96, such as a microprocessor unit, to perform the measurement e.g. according to the exemplary process shown in FIG. 8. A sample 94 is fed into the mixing chamber 90, and the light transmittance or absorbance may be first measured for the sample without the iodine solution. Then an iodine solution 95 may be fed into the mixing chamber 90 and mixed with the sample. After addition of the iodine solution, the light transmittance or absorbance may again be measured for the sample with the iodine solution. The difference in light transmittance or absorbance is related to starch concentration which may be calculated using a calibration curve in the controller 96, for example. The exemplary equipment will enable a fast and simple starch determination. A turbidity compensation can be automatically embedded in the calculations as the transmittance or absorbance of the sample is measured before and after Iodine addition.

In embodiments of the invention, in online measurement of the starch concentration the liquid samples conducted or taken, for example, from a pulp suspension or filtrate may comprise an essentially continuous sample stream or individual samples taken in sequences, e.g. at predetermined intervals. The individual sample may be a batch sample or "plug" of a predetermined size, such as from few millilitres to dozens of millilitres, preferably about 10 millilitres, taken with automated sampling means.

Figure 10:
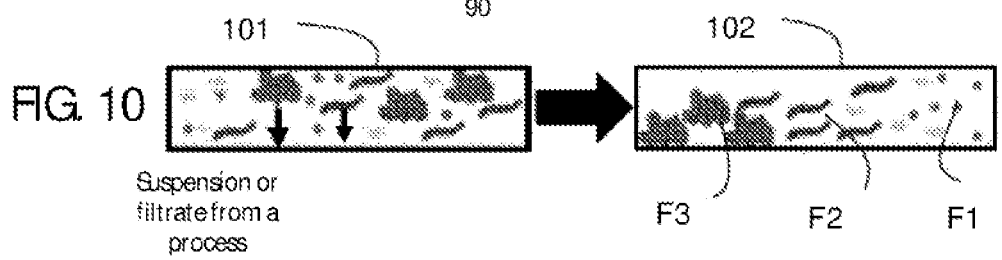
FIG. 10 illustrates a sample before and after fractionation.

In embodiments of the invention, different particle populations in the liquid samples such as pulp suspension or filtrate may be distinguished or separated from each other. For example, the suspended material in the liquid sample such as pulp suspension or filtrate may be separated or fractionated into one or more "fractions" according to the mass and/or size of the particles. For example, a fractionation may be performed by varying the water flow rate from a pump upstream of the sample to be fractionated, with the lightest particles coming out first, and the heaviest particles coming out last. As an example, FIG. 10 illustrates a sample before and after fractionation is shown. The unfractioned sample 101 contains, of course, a mix of particles of different sizes. Heavier particles have a tendency to sink, as shown by the arrows pointing downwards in 101. In a flow fractioned sample 102, the particles are divided into (at least) three particle populations F1, F2 and F3, the lightest particles F1 being first and the heaviest particles F3 being last in the sample. The very first fraction or population, preceding F1, may contain the dissolved liquid portion of the sample, including the dissolved starch, without particulate matter. The following fractions or populations of the sample may contain particles with absorbed starch. Thus, the different particle populations F1, F2 and F3 are coming out of the fractionator at different times, and the populations are therefore separated in time. The time needed to come out from the fractionator may be referred to as a retention time of the population. It can be seen that there is both a horizontal and vertical separation of the particle populations, the vertical difference being due to the difference in weight of the particles. The total amount of water used to fractionate the sample is generally not measured, but it is possible to determine the total amount of water based on pump speed and water flow rate data.

In embodiments of the invention, the sample containing particles is mixed with an iodine solution. The iodine concentration in a sample may be selected according to an application. Examples of different iodine concentrations in a sample are given above.

In embodiments of the inventions, the sample may be separated into one or more particle populations according to a particle size before the step of adding the iodine solution. A fraction or population may comprise the dissolved liquid portion of the sample, including the dissolved starch, without particulate matter.

In embodiments of the invention, starch concentration may be measured for one or more different fractions or particle populations. A fraction or population may comprise the dissolved liquid portion of the sample, including the dissolved starch, without particulate matter.

In embodiments of the invention, the light absorbance or transmittance of the sample may be measured for two or more different fractions or particle populations, and the measured absorbance or transmittance of the samples converted into the starch concentration of the sample for each particle population by means of a predefined correlation between the starch concentration and the light absorbance or transmittance.

In embodiments of the invention, the light absorbance or transmittance of the sample may be measured for two or more different fractions or particle populations both before and after the step of adding the iodine solution, a difference between the two measured absorbance or transmittance of the sample is converted into the starch concentration of the sample for each particle population by means of the predefined correlation between the starch concentration and the light absorbance or transmittance.

In embodiments of the invention, a number and a size of particles in fractions may be determined based a light scattering measurement or a turbidity measurement. Turbidity data may be used to determine the relative number of particles in each fraction. The turbidity (measured via a light scattering technique) of each fraction may depend upon, inter alia, the number of particles, the size of the respective particles, the shape of the respective particles, and the colour or reflectivity of the respective particles.

In embodiments of the invention, a ratio of dissolved and absorbed starch in the sample may be determined based on the starch concentrations of different particle populations.

Figure 11:
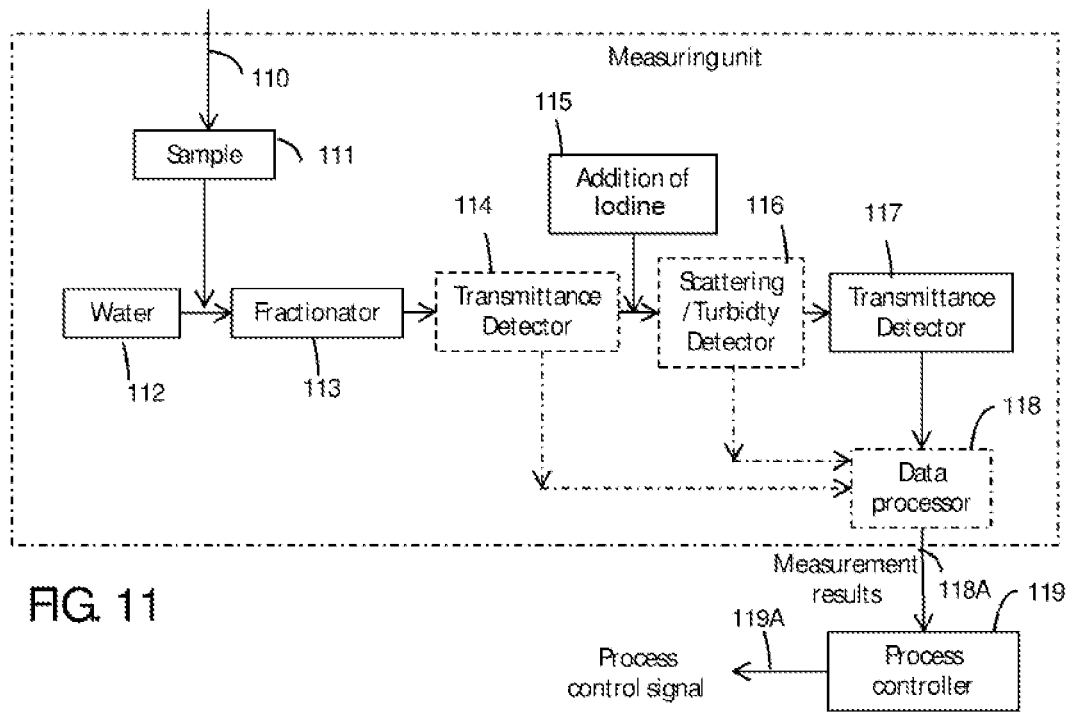
FIG. 11 shows a schematic block diagram of measurement equipment according to another exemplary embodiment.

FIG. 11 shows a schematic block diagram of exemplary measurement equipment according to another embodiment of the invention which particularly suitable for online measurement of starch. The measuring equipment may be considered to have two main parts: a preparation part and a measurement part. The preparation part may carry out sampling and separating the sample into particle populations. The preparation part may comprise a sample-taking device 111 that may be arranged to take, e.g. from a side flow 110 of the process suspension or filtrate, an essentially continuous sample stream or individual samples (such as a batch sample or "plug") of a predetermined size taken in sequences, e.g. at predetermined intervals. A source of fresh water 112 and a pump (not shown) may be provided for driving the sample or water forward through the fractionator 113 in the system using suitable valves (not shown). An iodine feed unit 115 (which may have an iodine reservoir) may be provided to feed the appropriate amount of iodine solution to the prepared sample from the preparation part, e.g. to fractioned sample flow from the fractionator 114. A transmittance/absorbance detector 117 may be arranged to measure a light absorbance or transmittance of the sample is measured at a wavelength longer than about 650 nm, preferably longer than about 700 nm, after adding the iodine solution. A further transmittance/absorbance detector 114 and/or a scattering or turbidity detector 116 may optionally be provided, as will be described in more detail below. The measurement part of the measuring equipment unit may also include a data processing unit 118 to carry out the processing of the measurement signals to provide the measurement results 119A. Alternatively, data processing 118 may be provided in a separate computing entity or computer, e.g. in the process controller 119 of a paper or board process. Such computing entity may be, for example, a programmable logic (PLC) or industrial computer for automatic operation of the system and data collection. The separate computing entity or computer, e.g. in the process controller 119 may further be arranged to provide an appropriate process control 119A to the process in question. A measurement unit which can be used for implementation of the measurement equipment 12 is an online measurement unit based on fractionation of the sample into one or more particle populations and measurement of particle populations by online sensors. For example, a fractionation of the sample may be performed by varying the water flow rate from a pump upstream of the sample to be fractioned, with the lightest particles coming out first and the heaviest particles coming out last. An example of such fractioning is disclosed in WO2013/175077.

The data processing unit 118 may be configured to convert the measured absorbance or transmittance of the sample into the starch concentration of the sample by means of a predefined correlation between a starch concentration and a light absorbance or transmittance. Such implementation would be in accordance with a procedure shown in FIG. 2, for example.

In an embodiment, a further transmittance/absorbance detector (a spectrometer) 114 may optionally be provided to measure a first light absorbance or transmittance of the prepared sample from the preparation part, e.g. from the fractioned sample flow from the fractionator 114, before addition of iodine. The measurement is made at a wavelength longer than about 650 nm, preferably longer than about 700 nm. The data processing unit 118 may be configured to convert a difference between the two measurements of absorbance or transmittance of the sample into the starch concentration of the sample by means of a predefined correlation between a starch concentration and a light absorbance or transmittance. Such implementation would be in accordance with a procedure shown in FIG. 8, for example.

According to an aspect of the invention, a turbidity of a sample may be measured and an effect of turbidity of the sample on the measurement of the absorbance or transmittance may be compensated based on the measured turbidity. This embodiment may be an alternative to a measurement of light absorbance or transmittance of the sample is measured at a wavelength longer than about 650 nm, preferably longer than about 700 nm both before and after adding an iodine solution to a sample. This may be applicable if turbidity meter was already available or was easier to implement than two light absorbance or transmittance measurements.

Referring to the exemplary measurement equipment shown in FIG. 11, a turbidity detector 116 may be optionally provided after the addition of iodine. The data processing unit 118 may be configured to compensate an effect of turbidity of the sample on the measurement of the absorbance or transmittance based on the measured turbidity, when the data processing unit 118 converts the measured absorbance or transmittance of the sample into the starch concentration of the sample by means of a predefined correlation between a starch concentration and a light absorbance or transmittance.

According to another aspect of the invention, a light scattering of the sample may be measured and an effect of turbidity of the sample on the measurement of the absorbance or transmittance may be compensated based on the light scattering measurement. This embodiment may be an alternative to a measurement of light absorbance or transmittance of the sample is measured at a wavelength longer than about 650 nm, preferably longer than about 700 nm both before and after adding an iodine solution to a sample.

Referring to the exemplary measurement equipment shown in FIG. 11, a scattering detector 116 may be optionally provided after the addition of iodine. The data processing unit 118 may be configured to compensate an effect of turbidity of the sample on the measurement of the absorbance or transmittance based on the measured scattering, when the data processing unit 118 converts the measured absorbance or transmittance of the sample into the starch concentration of the sample by means of a predefined correlation between a starch concentration and a light absorbance or transmittance.

This may be applicable if a scattering detector was already available or was easier to implement than two light absorbance or transmittance measurements. For example, in a measurement unit there may be a light scattering measurement which is also used for determining particle count/size in a sample. In an exemplary embodiment a change in transmittance or absorbance due to turbidity at the longer wavelengths may be predicted using the measured scattering signal. A prediction model may be provided that is a linear combination of random scattering values and transmittance or absorbance at the longer wavelengths measured from samples without added iodine. The predicted change in transmittance or absorbance due to the turbidity may then be cancelled from the transmittance or absorbance measurement. The resulting calibration may be sufficient in some applications.

In the following examples, an online starch concentration measurement according to principles of the invention was examined. The measurement apparatus was an online measurement unit based on fractionation of the sample into one or more particle populations and measurement of particle populations by online sensors. In these experiments only native starch was used, since the samples were fully bleached birch pulp prepared in laboratory. The pulp had very little fines as it was not refined and lacked fillers and other small particles present in real paper mill samples. As a result the fractionation produced only one particle population. The cationic wet-end starch could clearly be seen in these aggregates, however, the native starch acts as a much better example.

The iodine was fed at a constant rate to the sample feed just before the sample entered the spectrometer. The transmittance, i.e. the amount of light passing through the cell, was measured. As the absorption of iodine increases, the amount of light passing through the cell decreases. As shown earlier, free unreacted iodine will absorb light at 580 nm, but very little at 720 nm. In these experiments was used 754 nm.

Figure 12:
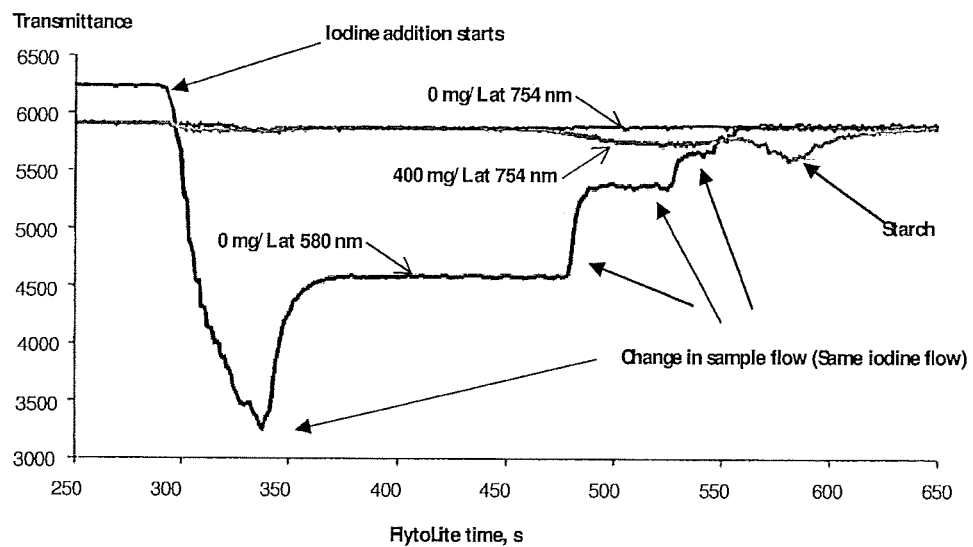
FIG. 12 shows a transmittance profile for a plain water (measured at 580 nm and 754 nm) and the sample with 400 mg/L starch added (measured at 754 nm)

FIG. 12 shows transmittance profile for a plain water (measured at 580 nm and 754 nm) and the sample with 400 mg/L starch added. The transmittance values are presented in function of time at iodine addition. It can be seen that the addition of iodine in plain water resulted in a significant reduction in the transmittance measured at 580 nm whereas the transmittance measured at 754 nm remain on approximately constant level. The change in transmittance of the starch sample measured at 754 nm was related to the amount of starch only.

Figure 13:
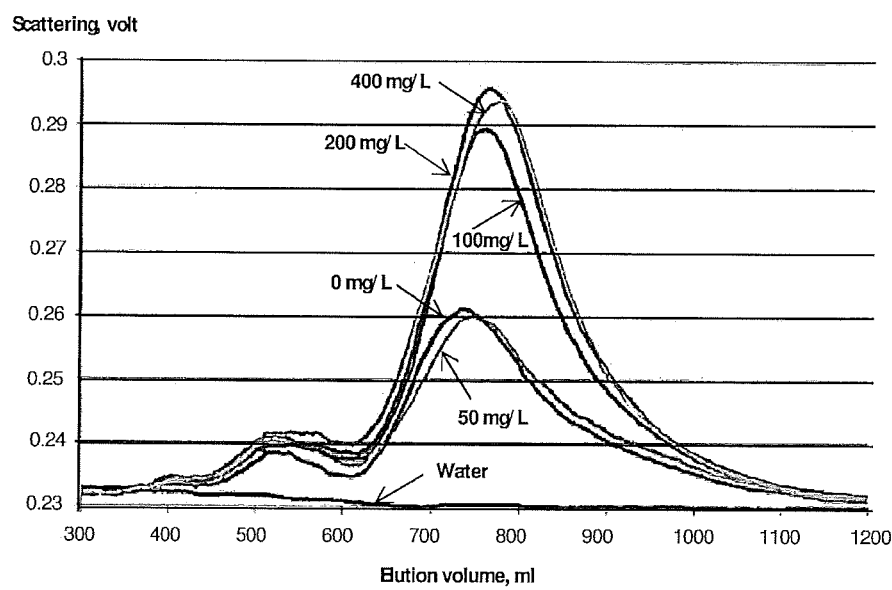
FIG. 13 shows a scattering profile of the pulp samples as a function of added native starch concentration.

FIG. 13 shows a scattering profile of the pulp samples as a function of added native starch concentration. The pulp consistency was 1% which makes the highest addition of 400 mg/L to be 40 kg/ton pulp. Above 100 mg/L the fibers became clearly more dispersed, which can explain the higher scattering for the fiber fraction.

FIG. 14 shows the transmittance change at 754 nm as a result of starch. The negative values are the result of the time shift inaccuracy between the scattering detector and the spectrometer. It can be clearly seen that the higher the amount of starch in the system the higher the transmittance reduction. It can also be seen that the amount of starch is mainly located in the small particles (before 560 seconds), but some is located in the fiber fraction (after 570 seconds). We can also see that the amount of starch in the fiber fraction increases clearly with the starch concentration above 100 mg/L, similarly to a change observed in the scattering profile.

If we summarize the transmittance change over the whole run (between 420 and 680 seconds) and plot this sum against the amount of added starch to the samples, we can derive in the graph shown in FIG. 15. FIG. 15 shows the true starch amount as a function of transmittance change. The results clearly demonstrate that a starch measurement method according to the invention also works for online measurement systems.

The change of the measurement from the traditional 580 nm to a higher wavelength, such as 740 nm, enables the use of a very simplified detector for starch determination. It is also clearly demonstrated that the measurement of starch in papermaking samples is possible and all the existing problems with the traditional method can be overcome. It is also demonstrated that the method is applicable for both online and laboratory use.

The method can be used to obtain an online value for the concentration of dissolved and absorbed starch in paper, board and tissue machines.

The method can be used for measurement of soluble starch but can also be extended to measure larger particles, such as fines, fibers and agglomerates.

The obtained concentration of dissolved and absorbed starch can be utilized for total chemistry management in paper, board and tissue processes. Typical applications may include retention, sizing, strength, deposit control and microbe control. Typical measuring locations may include wet end, broke line, pulp filtrates and long circulation.

The obtained concentration of dissolved and absorbed starch can be utilized for monitoring chemistry performance and controlling chemical dosages. Control can be manual or automatic.

It is to be understood that the embodiments of the invention disclosed are not limited to the particular structures, process steps, or materials disclosed herein, but are extended to equivalents thereof as would be recognized by those ordinarily skilled in the relevant arts.

It should also be understood that terminology employed herein is used for the purpose of describing particular embodiments only and is not intended to be limiting.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention. Well-known structures, materials, or operations are not shown or described in detail to avoid obscuring aspects of the invention.

Furthermore, the described features, structures, or characteristics may be combined in any suitable manner in one or more embodiments. In the following description, numerous specific details are provided, such as examples of lengths, widths, shapes, etc., to provide a thorough understanding of embodiments of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:

1. A method comprising;
    conducting a sample of liquid from a process stream of liquid for online analysis of a starch concentration in the process stream of liquid based on the sample of liquid;
    adding iodine solution to the sample of liquid;
    measuring a light absorbance or transmittance of the sample of liquid at a wavelength of 650 nm to 900 nanometers where unreacted iodine does not absorb light, after the step of adding the iodine solution;
    converting the measured absorbance or transmittance of the sample of liquid into the starch concentration of the sample of liquid by a predefined correlation between a starch concentration and a light absorbance or transmittance;
    wherein: the sample of liquid is conducted from a pulp suspension or filtrate in a paper, board or tissue process, and/or the method further comprises controlling a paper board or tissue process utilizing the starch concentration of the sample.

2. The method as claimed in claim 1, comprising:
    separating the sample of liquid into two or more particle populations according to a particle size and or mass before adding the iodine solution;
    measuring the light absorbance or transmittance of the sample of liquid for each particle population of the sample of liquid; and
    converting the measured absorbance or transmittance of the sample of liquid into the starch concentration of the sample of liquid for each particle population by the predefined correlation between the starch concentration and the light absorbance or transmittance.

3. The method as claimed in claim 2, wherein the said particle populations comprises:
    a population containing a liquid portion of the sample, including the dissolved starch, without particulate matter; and
    a population containing particles with absorbed starch.

4. The method as claimed in claim 2, wherein the one or more particle populations include:
    one or more of colloids, fines, fibers, floccules or agglomerates.

5. The method as claimed in claim 1, comprising:
    measuring a light scattering of the sample of liquid before and/or after adding the iodine solution; and
    compensating an effect of turbidity of the sample of liquid on the measurement of the absorbance or transmittance based on the light scattering measurement.

6. The method as claimed in claim 1, comprising:
    measuring a light scattering of the sample of liquid before and/or after adding the iodine solution; and
    determining a particle count in the sample of liquid based on the measured light scattering.

7. The method as claimed in claim 1, the method further comprising controlling the paper, board or tissue process utilizing the starch concentration of the sample, wherein the controlling comprises:
    one or more of retention control, sizing control, strength control, deposit control or microbe control.

8. The method as claimed in claim 1, wherein the starch comprises amylose and amylopectin.

9. The method of claim 1, comprising measuring the light absorbance or transmittance of the sample of liquid at a wavelength of 700 to 900 nanometers.

10. A method, comprising:
    conducting a sample of liquid from a process stream of liquid for online analysis of a starch concentration in the process stream of liquid based on the sample of liquid;
    adding iodine solution to the sample of liquid;
    measuring a light absorbance or transmittance of the sample of liquid at a wavelength of 650 to 900 nanometers both before and after adding the iodine solution to provide two measurements; and
    converting a difference between the two measurements of measured absorbance or transmittance of the sample of liquid into the starch concentration of the sample by a predefined correlation between a starch concentration and a light absorbance or transmittance;
    wherein: the sample of liquid is conducted from a pulp suspension or filtrate in a paper, board or tissue process, and/or the method further comprises controlling a paper, board or tissue process utilizing the starch concentration of the sample.

11. The method as claimed in claim 10, comprising:
    separating the sample of liquid into two or more particle populations according to a particle size and/or mass before adding the iodine solution;
    measuring the light absorbance or transmittance of the sample of liquid for each particle population of the sample of liquid both before and after adding the iodine solution; and
    converting a difference between the two measurements of measured absorbance or transmittance of the sample of liquid into the starch concentration of the sample of liquid for each particle population by the predefined correlation between the starch concentration and the light absorbance or transmittance.

12. The method as claimed in claim 11, wherein the said particle populations comprises:
    a population containing a liquid portion of the sample, including the dissolved starch, without particulate matter; and
    a population containing particles with absorbed starch.

13. The method as claimed in claim 11, wherein the one or more particle populations include:
    one or more of colloids, fines, fibers, floccules or agglomerates.

14. The method as claimed in claim 10, comprising:
    measuring a light scattering of the sample of liquid before and/or after adding the iodine solution; and
    compensating an effect of turbidity of the sample of liquid on the measurement of the absorbance or transmittance based on the light scattering measurement.

15. The method as claimed in claim 10, comprising:
  measuring a light scattering of the sample of liquid before and/or after adding the iodine solution; and
  determining a particle count in the sample of liquid based on the measured light scattering.

16. The method as claimed in claim 10, further comprising:
  controlling the paper, board or tissue process utilizing the starch concentration of the sample, wherein the controlling comprises:
  one or more of retention control, sizing control, strength control, deposit control or microbe control.

17. The method of claim 10, comprising measuring the light absorbance or transmittance of the sample of liquid at a wavelength of 700 to 900 nanometers.

* * * * *